United States Patent [19]

Sircar et al.

[11] Patent Number: 4,554,282

[45] Date of Patent: Nov. 19, 1985

[54] SUBSTITUTED 2,2-DIMETHYL-5-PHENOXYPENTANOIC ACID BENZAMIDES AS ANTI-ARTERIOSCLEROTIC AGENTS AND METHOD

[75] Inventors: Ila Sircar, Ann Arbor; Ann Holmes, Dexter, both of Mich.

[73] Assignee: Warner-Lambert Company, Morris Plains, N.J.

[21] Appl. No.: 520,874

[22] Filed: Aug. 5, 1983

Related U.S. Application Data

[62] Division of Ser. No. 238,398, Feb. 26, 1981, Pat. No. 4,413,011.

[51] Int. Cl.$^4$ .................. C07C 143/80; C07D 213/34; A61K 31/18; A61K 31/44
[52] U.S. Cl. ..................................... 514/357; 514/603; 514/824; 546/304; 546/329; 546/334; 564/86; 564/175
[58] Field of Search .................. 564/86, 175; 546/304, 546/329, 334; 424/263, 321, 324; 514/357, 603, 824

[56] References Cited

U.S. PATENT DOCUMENTS

| 3,723,524 | 3/1973 | Augstein et al. | 564/86 X |
| 3,878,212 | 4/1975 | Rufer et al. | 564/86 X |
| 4,413,011 | 11/1983 | Sircar et al. | 424/324 X |

FOREIGN PATENT DOCUMENTS

| 0059855 | 4/1982 | Japan | 564/86 |
| 7204506 | 10/1972 | Netherlands | 564/86 |

*Primary Examiner*—Thomas A. Waltz
*Attorney, Agent, or Firm*—Jerry F. Janssen

[57] ABSTRACT

New substituted 2,2-dimethyl-5-phenoxypentanoic acid benzamides which are useful as anti-arteriosclerotic agents are disclosed. These compounds elevate the high density lipoprotein fraction of cholesterol, and also lower the low density lipoprotein fraction of cholesterol.

8 Claims, No Drawings

SUBSTITUTED 2,2-DIMETHYL-5-PHENOXYPENTANOIC ACID BENZAMIDES AS ANTI-ARTERIOSCLEROTIC AGENTS AND METHOD

This is a division of application Ser. No. 238,398 filed Feb. 26, 1981, now U.S. Pat. No. 4,413,011.

BACKGROUND OF THE INVENTION

Elevated levels of blood cholesterol and blood lipids are conditions which are believed related to the onset of arteriosclerosis. Thus, compounds capable of reducing the levels of these blood constituents are recognized as potentially useful anti-arteriosclerotic agents.

The compounds of the present invention are useful as anti-arteriosclerotic agents and are capable of elevating the high density lipoprotein fraction of cholesterol (HDL-cholesterol,) which effect is known to lower the risk factor of coronary heart disease (Gordon, T. et al., High Density Lipoprotein as a Protective Factor Against Coronary Heart Disease, May 1977, *The American Journal of Medicine*, Vol. 62, pp. 707-714). Certain compounds of the invention also are able to reduce the low density lipoprotein fraction of cholesterol (LDL-cholesterol), thus further reducing the risk factor of coronary heart disease.

SUMMARY OF THE INVENTION

The invention sought to be patented in its generic compound aspect is a compound having the structural formula:

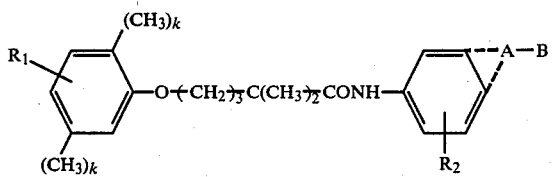

wherein $R_1$ is hydrogen, hydroxy, alkyl of from 1 to 6 carbon atoms, alkoxy of from 1 to 6 carbon atoms, benzyloxy or trifluoromethyl; $R_2$ is hydrogen, hydroxy, halogen, alkyl of from 1 to 6 carbon atoms or alkoxy of from 1 to 6 carbon atoms; A is $(CH_2)_m$ wherein m is an integer of from 0-3, $(CR_4=CR_5)_n$ wherein $R_4$ and $R_5$ are trans to each other and are hydrogen or alkyl of from 1 to 6 carbon atoms n is 0 or 1, and the dotted lines indicate the presence of only one substituent which must be located at one of the specified positions; B is (1) $CH_2OH$, CHO, $COR_3$ wherein $R_3$ is alkyl of from 1 to 6 carbon atoms, or $CO_2X$ wherein X is hydrogen, alkyl of from 1 to 6 carbon atoms, ammonium or a pharmaceutically acceptable metal or organic amine cation; or (2) $SO_2NHR_6$ wherein $R_6$ is hydrogen; alkyl of from 1 to 6 carbon atoms; or

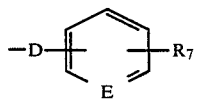

wherein
D is a bond or an alkylene group of from 1 to 6 carbon atoms, E is CH or N and $R_7$ is hydrogen, alkyl of from 1 to 6 carbon atoms, alkoxy of from 1 to 6 carbon atoms or halogen;

k is 0 or 1 with the proviso that when k is O, $R_1$ may not be alkyl of from 1 to 6 carbon atoms and when k is 1, $R_1$ must be in the 4-position.

The invention sought to be patented in a preferred subgeneric compound aspect is a compound having the structural formula:

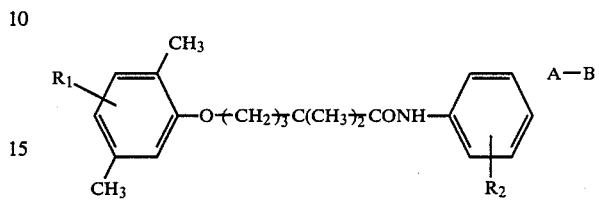

wherein $R_1$ is hydrogen, hydroxy, alkoxy of from 1 to 6 carbon atoms, benzyloxy or trifluoromethyl; $R_2$ is hydrogen, hydroxy, halogen, alkyl of from 1 to 6 carbon atoms or alkoxy of from 1 to 6 carbon atoms; A is $(CH_2)_m$ wherein m is an integer of from 0-3, $(CR_4=CR_5)_n$ wherein $R_4$ and $R_5$ are trans to each other and are hydrogen or alkyl of from 1 to 6 carbon atoms n is 0 or 1, and the dotted lines indicate the presence of only one substituent which must be located at one of the specified positions;

(1) $CH_2OH$, CHO, $COR_3$ wherein $R_3$ is alkyl of from 1 to 6 carbon atoms, or $CO_2X$ wherein X is hydrogen, alkyl of from 1 to 6 carbon atoms, ammonium or a pharmaceutically acceptable metal or organic amine cation; or (2) $SO_2NHR_6$ wherein $R_6$ is hydrogen; alkyl of from 1 to 6 carbon atoms; or

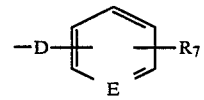

wherein D is a bond or an alkylene group of from 1 to 6 carbon atoms, E is CH or N and $R_7$ is hydrogen, alkyl of from 1 to 6 carbon atoms, alkoxy of from 1 to 6 carbon atoms or halogen.

The invention sought to be patented in a first specific compound aspect is the compound having the structural formula:

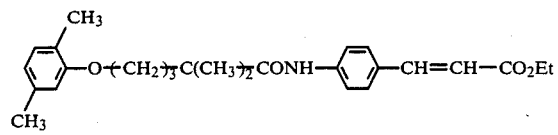

The invention sought to be patented in a second specific compound aspect is the compound having the structural formula:

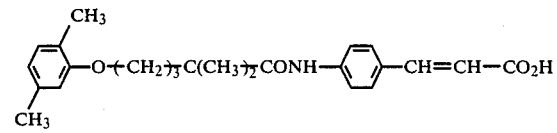

The invention sought to be patented in a third specific compound aspect is the compound having the structural formula:

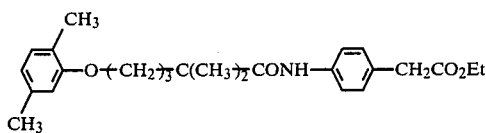

The invention sought to be patented in a fourth specific compound aspect is the compound having the structural formula:

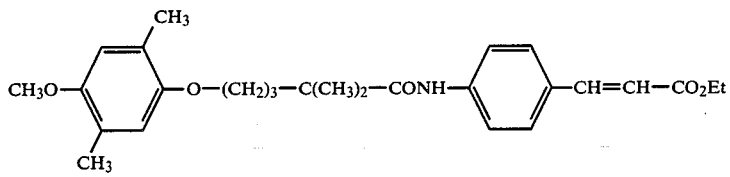

The invention sought to be patented in a fifth specific compound aspect is the compound having the structural formula:

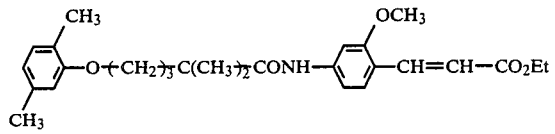

The invention sought to be patented in a sixth specific compound aspect is the compound having the structural formula:

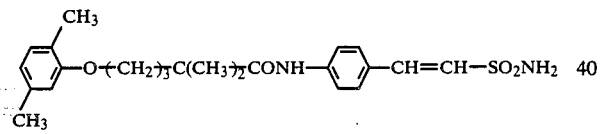

The invention sought to be patented in a chemical process aspect is a process for preparing a compound having the structural formula:

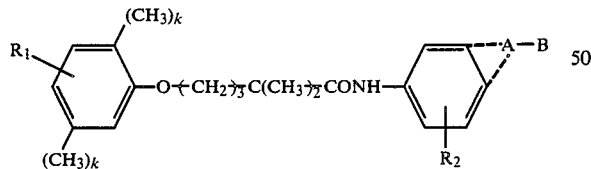

wherein $R_1$ is hydrogen, hydroxy, alkyl of from 1 to 6 carbon atoms, alkoxy of from 1 to 6 carbon atoms, benzyloxy or trifluoromethyl; $R_2$ is hydrogen, hydroxy, halogen, alkyl of from 1 to 6 carbon atoms or alkoxy of from 1 to 6 carbon atoms; A is $(CH_2)_m$ wherein m is an integer of from 0-3, $(CR_4=CR_5)_n$ wherein $R_4$ and $R_5$ are trans to each other and are hydrogen or alkyl of from 1 to 6 carbon atoms n is 0 or 1, and the dotted lines indicate the presence of only one substituent which must be located at one of the specified positions; B is (1) $CH_2OH$, CHO, $COR_3$ wherein $R_3$ is alkyl of from 1 to 6 carbon atoms, or $CO_2X$ wherein X is hydrogen, alkyl of from 1 to 6 carbon atoms, ammonium or a pharmaceutically acceptable metal or organic amine cation; or (2) $SO_2NHR_6$ wherein $R_6$ is hydrogen; alkyl of from 1 to 6 carbon atoms; or

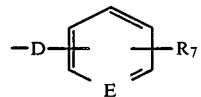

wherein
D is a bond or an alkylene group of from 1 to 6 carbon atoms, E is CH or N and $R_7$ is hydrogen, alkyl of from 1 to 6 carbon atoms, alkoxy of from 1 to 6 carbon atoms or halogen;
k is 0 or 1 with the proviso that when k is 0, $R_1$ may not be alkyl of from 1 to 6 carbon atoms and when k is 1, $R_1$ must be in the 4-position; which comprises (a) reacting a compound having the structural formula:

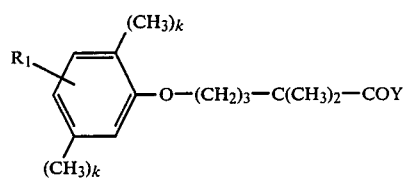

with a compound having the structural formula:

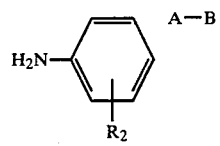

wherein $R_1$, $R_2$ A, B, the dotted lines and k have the meanings as defined above, and Y is hydroxy, chlorine, bromine, an active ester or an anhydride; and (b) isolating the product.

The invention sought to be patented in a pharmaceutical composition aspect is a composition useful for treating arteriosclerosis in a mammal consisting essentially of a compound having the structural formula I or mixtures thereof, in combination with a pharmaceutically acceptable carrier.

The invention sought to be patented in a pharmaceutical method aspect is a method for treating arteriosclerosis in a mammal in need of such treatment; which comprises administering an effective amount of the above defined pharmaceutical composition to said mammal.

DESCRIPTION OF THE PREFERRED EMBODIMENTS

The compounds of the invention may be prepared by any of several processes which are to be considered as equivalent for purposes of this invention.

One such process involves the reaction between an acid having the structural formula IV,

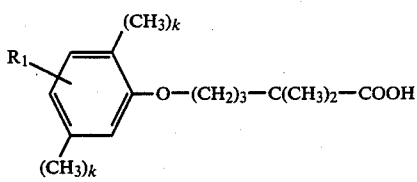

with a substituted aniline having the structural formula III,

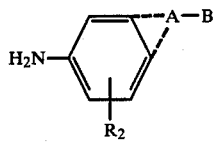

Those skilled in the art will appreciate that compounds III and IV may be directly reacted with the aid of such reagents as dicyclohexylcarbodiimide and the like. More preferably, the acids of structural formula IV are first converted to a reactive derivative such as an activated ester, anhydride or an acid halide and then reacted with the aniline of formula III by known procedures. For example, an acid halide such as the chloride or bromide corresponding to the acid having structural formula IV may be contacted in a suitable solvent with an aniline having structural formula III in the presence of an acid acceptor such as a tertiary amine or an alkali or alkaline earth metal carbonate or bicarbonate. When preparing compounds of the invention wherein substituted B is other than $SO_2NHR_6$, substituent B of compound III is preferably in the form of an ester during the reaction, this for reasons of convenience and better yields. The ester substituent may subsequently be removed, e.g., by dilute basic hydrolysis, and the carboxylic acid substituent so produced may be converted to one of the other contemplated substituents, B by known methods. Alternatively, substituent B may already be present as a $CH_2OH$, $CHO$, or $CO$-lower alkyl group in either a protected or free form. For example, the aldehyde or ketone carbonyl group may be present as an acetal or ketal, such as an ethylene ketal, which protecting group may be removed by dilute acid hydrolysis after the condensation reaction is completed.

The acid halides corresponding to the acids having structural formula IV may be prepared by known methods. Thus, for example, the acid halides may be prepared by treating the acids with any of the common halogenating reagents such as phosphorous pentachloride, phosphorous oxybromide, thionyl chloride, oxalyl chloride and the like. The preferred reagent is oxalyl chloride.

The activated esters and anhydrides contemplated by the invention are well known carboxylic acid derivatives and may be prepared by methods known to those skilled in the art.

The carboxylic acids having structural formula IV may be prepared by the procedures described in U.S. Pat. No. 3,674,836. The anilines having structural formula III are either commercially available or may be prepared by known methods or obvious variations thereof. Compounds having structural formula III wherein A is CH=CH may be prepared by the procedures described in Swiss Pat. No. 287,557 [C.A. 49, 2505g (1955)] and Swiss Pat. No. 294,942 [C.A. 50 4219f (1956)].

The compounds of the invention wherein B is COOH, or $SO_2NHR_6$ are acidic in nature and form pharmaceutically acceptable salts with both organic and inorganic bases. Examples of such bases are sodium hydroxide, sodium carbonate, sodium bicarbonate, potassium hydroxide, calcium hydroxide, ammonia, organic amines and the like. The salts are prepared by contacting the free acid form with an equivalent amount of the desired base in the conventional manner. The free acid forms may be regenerated by treating the salt form with an acid. For example, dilute aqueous acid solutions may be utilized. Dilute aqueous hydrochloric acid, sulfuric acid or acetic acid are suitable for this purose. The free acid forms differ from their respective salt forms somewhat in certain physical properties such as solubility in polar solvents, but the salts are otherwise equivalent to their respective free acid forms for purposes of the invention.

The compounds of the invention can exist in unsolvated as well as solvated forms, including hydrated forms. In general, the solvated forms with pharmaceutically acceptable solvents such as water, ethanol and the like are equivalent to the unsolvated forms for purposes of the invention.

The alkyl groups, alkoxy groups and alkylene groups contemplated by the invention comprise both straight and branched carbon chains of from 1 to about 6 carbon atoms. Representative of such groups are methyl, ethyl, isopropyl, pentyl, 3-methylpentyl, methoxy, ethoxy, propoxy, 1-ethylbutoxy, pentoxy, methylene, ethylene, propylene, 2-methylbutylene, 2-ethylbutylene and the like.

The term halogen is intended to include fluorine, chlorine, bromine and iodine.

Pharmaceutically acceptable metal cations are intended to include the cations of the alkali and alkaline earth metals, e.g., sodium, potassium, magnesium, calcium and the like; also intended is aluminum and the cations of other pharmaceutically compatible metals. Pharmaceutically acceptable amine cations are the positively charged ammonium, substituted-ammonium and cyclic ammonium ions derived from organic nitrogenous bases strong enough to form such cations. Illustrative of such cations are ammonium, mono-, di- and tri-alkylammonium, cyclohexylammonium, benzylammonium, piperidinium, morpholinium, pyrrolidinium, pyridinium, and the like.

The compounds of the invention are new chemical substances of value as pharmacological agents for the treatment of arteriosclerosis in warm-blooded animals. The anti-arteriosclerotic activity of representative compounds of the invention was established by the Screening procedure described in Maxwell, R. E., Nawrocki, J. W., and Uhlendorf, P. D., Artery, 1, 303 (1978). This procedure is incorporated by reference herein. Utilizing this procedure, the following results were obtained for representative compounds of this invention.

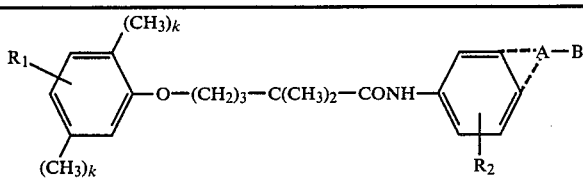

| k | $R_1$ | $R_2$ | A | B | % Change in HDL | % Change in Liver Weight | % Change in LDL |
|---|---|---|---|---|---|---|---|
| 1 | H | H | 4'-bond | $CO_2Et$ | +147 | 0 | −23 |
| 1 | H | H | 3'-bond | $CO_2H$ | +341 | +7 | −32 |
| 1 | H | 3'-OH | 4'-bond | $CO_2H$ | +313 | +14 | −28 |
| 1 | H | H | 4'$CH_2$ | $CO_2Et$ | +385 | 0 | −26 |
| 1 | H | H | 4'(CH=CH) | $CO_2Et$ | +212 | 0 | 0 |
| 0 | H | H | 4'(CH=CH) | $CO_2Et$ | +88 | 0 | −10 |
| 0 | 3-$CF_3$ | H | 4'(CH=CH) | $CO_2Et$ | +279 | +8 | 0 |
| 1 | 4-OMe | H | 4'(CH=CH) | $CO_2Et$ | +580 | +11 | −21 |
| 1 | 4-$OCH_2Ph$ | H | 4'(CH=CH) | $CO_2Et$ | +100 | 0 | −20 |
| 1 | 4-OH | H | 4'(CH=CH) | $CO_2Et$ | +174 | +7 | 0 |
| 1 | H | H | 3'(CH=CH) | $CO_2Et$ | +280 | 0 | −19 |
| 1 | H | H | 4'($CH_2CH_2$) | $CO_2Et$ | +216 | +7 | 0 |
| 1 | H | 3'-OMe | 4'(CH=CH) | $CO_2Et$ | +372 | 0 | −18 |
| 1 | H | 3'-Cl | 4'(CH=CH) | $CO_2Et$ | +279 | +16 | −26 |
| 1 | H | H | 4'(CH=CH) | $SO_2NH_2$ | +374 | 0 | −29 |

An increase in liver weight is indicative of hepatomegaly and hepatic peroxisome proliferation. Both are undesirable side effects of the known anti-artereosclerotic agents, Reddy, J. K; and Krishnakantha, T. P., Science, 190, 787 (1975).

The compounds of the invention can be prepared and administered in a wide variety of oral and parenteral dosage forms. It will be clear to those skilled in the art that the following dosage forms may comprise as the active component, either a compound of formula I, or a correspondingly pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be n encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelaatin, tragacanth, methyl cellulose, sodium carboxymethyl cellulose, a low melting wax, cocoa butter and the like, The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl cellulose and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these packaged form.

The quantity of active compound in a unit dose of preparation may be varied or adjusted from 1 mg to 100 mg according to the particular application and the potency of the active ingredient.

In therapeutic use as agents for treating arteriosclerosis, the compounds utilized in the pharmaceutical method of this invention are administered at the initial dosage of about 10 mg to about 250 mg per kilogram daily. A daily dose range of about 10 mg to about 30 mg per kilogram is preferred. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following non-limiting examples illustrate the inventor's preferred methods for preparing the compounds of the invention.

EXAMPLE 1

A solution of oxalyl chloride (4.4 ml) in toluene (100 ml) is added dropwise to a solution of 5-(2,5-dimethylphenoxy)-2,2-dimethylvaleric acid (6.25 g) in toluene (50 ml) at 0° C. with stirring. The solution is stirred for an additional 30 minutes at 0° C. followed by stirring at room temperature for three to four hours. Toluene is distilled off under reduced pressure, the residue is dissolved in $CH_2Cl_2$ (60 ml) and is added to a solution of ethyl 4-aminobenzoate (4.3 g) in $CH_2Cl_2$ (60 ml) containing $Et_3N$ (2.5 g) at ambient temperature. The solution is stirred overnight, followed by washing successively with water, dilute hydrochloric acid, dilute sodium bicarbonate, and water. The solution is dried over anhydrous $MgSO_4$, stripped to dryness, and crystallized from isopropyl ether yielding 8.2 g of the product, ethyl 4-[[5-(2,5-dimethylphenoxy)-2,2-dimethyl-1-oxopentyl]amino]-benzoate; mp 90° C.

EXAMPLE 2

Following the procedure of Example 1, with the substitution of ethyl 3-aminobenzoate in place of ethyl 4-aminobenzoate, the product obtained is ethyl 3-[[5-(2,5-dimethylphenoxy)-2,2-dimethyl-1-oxopentyl]amino]benzoate which was saponified to give 3-[[5-(2,5-dimethylphenoxy)-2,2-dimethyl-1-oxopentyl)amino]benzoic acid; mp 161° C. following crystallization from tetrahydrofuran-isopropyl ether.

EXAMPLE 3

Following the procedure of Example 1, with the substitution of 4-amino-2-hydroxybenzoic acid in place of ethyl 4-aminobenzoate, the product obtained is 4-[[5-(2,5-dimethylphenoxy)-2,2-dimethyl-1-oxopentyl]amino]-2-hydroxy benzoic acid; mp 205°–207° C. dec, following crystallization from tetrahydrofuran-isopropyl ether.

EXAMPLE 4

Following the procedure of Example 1, with the substitution of ethyl 4-aminobenzeneacetate in place of ethyl 4-aminobenzoate, the product obtained is ethyl 4-[[5-(2,5-dimethylphenoxy)-2,2-dimethyl-1-oxopentyl]amino]-benzeneacetate; mp 61°–64° C. following crystallization from ethanol-water.

EXAMPLE 5

5-(2,5-dimethylphenoxy)-2,2-dimethylvaleric acid (6.25 g) is converted to the corresponding acid chloride by the action of oxalyl chloride as in the Example 1. The above acid chloride is dissolved in THF (60 ml) and is added to a solution of ethyl 4-aminocinnamate (4.7 g) in THF (60 ml) containing $Et_3N$ (2.5 g) at ambient temperature followed by stirring overnight. The inorganic solid is filtered off and the filtrate is evaporated to dryness to yield 9.5 g of the product ethyl 3-[4-[[5-(2,5-dimethylphenoxy)-2,2-dimethyl-1-oxopentyl]amino]phenyl]-2-propenoate; mp 101°–102° C. following crystallization from isopropyl ether.

EXAMPLE 6

5.43 g of ethyl 3-[4-[[5-(2,5-dimethylphenoxy)-2,2-dimethyl-1-oxopentyl]amino]phenyl]-2-propenoate is agitated with 2N methanolic sodium hydroxide (32 ml) overnight at room temperature. After usual work up, the product obtained is 3-[4-[[5-(2,5-dimethylphenoxy)-2,2-dimethyl-1-oxopentyl]amino]phenyl]-2-propenoic acid (4.36 g); mp 161.5°–162.5° C. following crystallization from methylene chloride-isopropylether.

EXAMPLE 7

Following the procedure of Example 5, with the substitution of ethyl 3-aminocinnamate in place of ethyl 4-aminocinnamate, the product obtained is ethyl 3-[3-[[5-(2,5-dimethylphenoxy)-2,2-dimethyl-1-oxopentyl]amino]phenyl]-2-propenoate; mp 84°–85° C. following crystallization from isopropyl ether.

EXAMPLE 8

Following the procedure of Example 5, with the substitution of 5-phenoxy-2,2-dimethylvaleric acid in place of 5-(2,5-dimethylphenoxy)-2,2-dimethylvaleric acid, the product obtained is ethyl 3-[4-[(2,2-dimethyl-1-oxo-5-phenoxypentyl)amino]phenyl]-2-propenoate; mp 151°–152° C. following crystallization from isopropyl ether.

EXAMPLE 9

Following the procedure of Example 5, with the substitution of 5-(3-trifluoromethylphenoxy)-2,2-dimethylvaleric acid in place of 5-(2,5-dimethylphenoxy)-2,2-dimethylvaleric acid, the product obtained is ethyl 3-[4-[[2,2-dimethyl-1-oxo-5-[3-(trifluoromethyl)phenoxy]pentyl]amino]phenyl]-2-propenoate; mp 96°–97° C. following crystallization from isopropyl ether.

EXAMPLE 10

Following the procedure of Example 5, with the substitution of 5-(2,5-dimethyl-4-methoxyphenoxy)-2,2-dimethylvaleric acid in place of 5-(2,5-dimethylphenoxy)-2,2-dimethylvaleric acid, the product obtained is ethyl 3-[4-[[5-(2,5-dimethyl-4-methoxyphenoxy)-2,2-dimethyl-1-oxopentyl]amino]phenyl]-2-propenoate; mp 95°–96° C. following crystallization from isopropyl alcohol.

EXAMPLE 11

Following the procedure of Example 5, with the substitution of 5-(2,5-dimethyl-4-phenylmethoxyphenoxy)-2,2-dimethylvaleric acid in place of 5-(2,5-dimethylphenoxy)-2,2-dimethylvaleric acid, the product obtained is ethyl 3-[4-[[5-[2,5-dimethyl-4-(phenylmethoxy)phenoxy]-2,2-dimethyl-1-oxopentyl]amino]phenyl]-2-propenoate; mp 121°–122° C. following crystallization from isopropyl ether.

EXAMPLE 12

Following the procedure of Example 5, with the substitution of 5-(2,5-dimethyl-4-tetrahydropyranyloxyphenoxy)-2,2-dimethylvaleric acid in place of 5-(2,5-dimethylphenoxy)-2,2-dimethylvaleric acid, the product obtained is ethyl 3-[4-[[5-(4-hydroxy-2,5-dimethylphenoxy)-2,2-dimethyl-1-oxopenyl]amino]phenyl]-2-propenoate following hydrolysis of the initial reaction product; mp 122°–124° C.

EXAMPLE 13

Following the procedure of Example 5, with the substitution of ethyl 2-chloro-4-aminocinnamate in place of ethyl 4-aminocinnamate, the product obtained is ethyl 3-[2-chloro-4-[[5-(2,5-dimethylphenoxy)-2,2-dimethyl-1-oxopentyl]amino]phenyl]-2-propenoate.

EXAMPLE 14

Following the procedure of Example 5, with the substitution of ethyl 2-methyl-4-aminocinnamate in place of ethyl 4-aminocinnamate, the product obtained is ethyl 3-[4-[[5-(2,5-dimethylphenoxy)-2,2-dimethyl-1-oxo-pentyl]amino]-2-methylphenyl]-2-propenoate; mp 73°-74° C., following crystallization from isopropyl ether.

EXAMPLE 15

Following the procedure of Example 5, with the substitution of ethyl 3-hydroxy-4-aminocinnamate in place of ethyl 4-aminocinnamate, the product obtained is ethyl 3-[4-[[5-(2,5-dimethylphenoxy)-2,2-dimethyl-1-oxopentyl]amino]-3-hydroxyphenyl]-2-propenoate; mp 134°-135° C., following crystallization from methylene chloride and isopropyl ether.

EXAMPLE 16

Following the procedure of Example 5, with the substitution of ethyl 2-methoxy-4-aminocinnamate in place of ethyl 4-aminocinnamate, the product obtained is ethyl 3-[4-[[5-(2,5-dimethylphenoxy)-2,2-diemethyl-1-oxopentyl]amino]-2-methoxyphenyl]-2-propenoate.

EXAMPLE 17

0.84 g of ethyl 3-[3-[[5-(2,5-dimethylphenoxy)-2,2-dimethyl-1-oxopentyl]amino]phenyl]-2-propenoate, is reduced catalytically to give 0.6 g of the product ethyl 3-[[5-(2,5-dimethylphenoxy)-2,2-dimethyl-1-oxopentyl]amino]benzenepropanoate; mp 69° C. following crystallization from ether.

EXAMPLE 18

4.9 g of ethyl 3-[4-[[5-(2,5-dimethylphenoxy)-2,2-dimethyl-1-oxopentyl]amino]phenyl]-2-propenoate is reduced catalytically to give 4.3 g of the product ethyl 4-[[5-(2,5-dimethylphenoxy)-2,2-dimethyl-1-oxopentyl]amino]benzenepropenoate; mp 79°-80° C. following crystallization from isopropyl ether.

EXAMPLE 19

5-(2,5-Dimethylphenoxy)-2,2-dimethylvaleric acid is converted to the corresponding acid chloride by the action of oxalyl chloride as in Example 1. The acid chloride is dissolved in THF (250 ml) and is added to a solution of 1-p-aminophenyl)ethene-1-sulfonamide (40.1 g), prepared by the catalytic reduction of 2-(p-nitrophenyl)ethene-1-sulfonamide [prepared by the procedure described in *J. Am. Chem. Co.,* 68 1778 (1946)], in THF (250 ml) containing Et$_3$N (20.45 g). Stir at ambient temperature overnight. The inorganic solid is filtered off and the filtrate concentrated to dryness in vacuo to give an oil that quickly solidifies when treated with water. The product, N-[4-[2-(aminosulfonyl)ethenyl]-phenyl-5-(2,5-dimethylphenoxy)-2,2-dimethylpentanamide, is recrystallized from isopropanol to yield 41.2 g; mp 152°-153° C.

EXAMPLE 20

Following the procedure of Example 19 with the substitution of 3-aminobenzenesulfonamide in place of 2-(p-aminophenyl)ethene-1-sulfonamide, the product obtained is N-[3-(aminosulfonyl)phenyl]-5-(2,5-dimethylphenoxy)-2,2-dimethylpentanamide; mp 179°-180° C. following crystallization from aqueous ethanol.

EXAMPLE 21

Following the proedure of Example 19 with the substitution of 4-aminobenzenesulfonamide in place of 2-(p-aminophenyl)ethene-1-sulfonamide, the product obtained is N-[4-(aminosulfonyl)phenyl]-5-(2,5-dimethylphenoxy)-2,2-dimethylpentanamide; mp 146°-147° C. following crystallization from aqueous ethanol.

EXAMPLE 22

Following the procedure of Example 19 with the substitution of p-aminomethylbenzenesulfonamide in place of 2-(p-aminophenyl)ethene-1-sulfonamide, the product obtained is N-[[4-(aminosulfonyl)phenylmethyl]-5-(2,5-dimethylphenoxy)]-2,2-dimethylpentanamide; mp 112°-113° C. foiowing crystallization from aqueous ethanol.

EXAMPLE 23

Following the procedure of Example 19 with the substitution of 2-(p-aminophenyl)ethene-1-N-t-butylsulfonamide in place of 2-(p-aminophenyl)ethene-1-sulfonamide, the product obtained is N-[4-[2-(N-t-butylaminosulfonyl)-ethyl]phenyl]-5-(2,5-dimethylphenoxy)-2,2-dimethylpentanamide; mp 97°-98° C. following crystallization from aqueous ethanol.

EXAMPLE 24

Following the procedure of Example 19 with the substitution of 4-amino-N-methylbenzenesulfonamide in place of 2-(p-aminophenyl)ethene-1-sulfonamide, the product obtained is 5-(2,5-dimethylphenoxy)-N-[[4-(methylamino)sulfonyl]phenyl]-2,2-dimethylpentanamide; mp 125°-127° C. following crystallization from aqueous ethanol.

EXAMPLE 25

Following the procedure of Example 19 with the substitution of 4-amino-N-(3-pyridylmethyl)benzenesulfonamide in place of 2-(p-aminophenyl)ethene-1-sulfonamide, the product obtained is N-[4-(N-(3-pyridylmethylamino)sulfonyl)phenyl]-5-(2,5-dimethylphenoxy)-2,2-dimethylpentanamide; mp 150°-151° C. following crystallization from aqueous ethanol.

EXAMPLE 26

Following the procedure of Example 19 with the substitution of 5-amino-2-methoxybenzenesulfonamide in place of 2-(p-aminophenyl)ethene-1-sulfonamide, the product obtained is N-[3-(aminosulfonyl)-4-methoxyphenyl]-5-(2,5-dimethylphenoxy)-2,2-dimethylpentanamide; mp 124°-125° C. following crystallization from aqueous ethanol.

EXAMPLE 27

Following the procedure of Example 19 with the substitution of 5-amino-2-methoxy-N-methylbenzenesulfonamide in place of 2-(p-aminophenyl)ethene-1-sulfonamide, the product obtained is 5-(2,5-dimethylphenoxy)-N-[4-methoxy-3-[(methylamino)sulfonyl]-phenyl]-2,2-dimethylpentanamide; mp 140°-142° C. following crystallization from aqueous ethanol.

EXAMPLE 28

Followng the procedure of Example 19 with the substitution of 5-amino-2-methylamino-N-methylbenzenesulfonamide in place of 2-(p-aminophenyl)ethene-1-sulfonamide, the product obtained is 5-(2,5-dimethylphenoxy)-N-[4-methylamino-3-[(methylamino)sulfonyl]phenyl]-2,2-dimethylpentanamide; mp 112°–114° C. following crystallization from aqueous ethanol.

We claim:

1. A compound having the structural formula

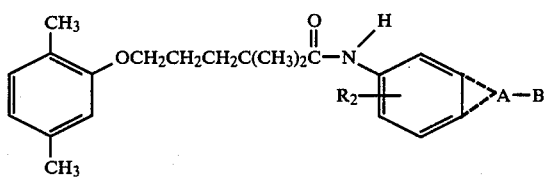

wherein the dotted lines indicate the presence of only one substituent which must be located at one of the specified positions, and (a) A is $-CR_4=CR_5-$, where $R_4$ and $R_5$ are are trans to each other and are hydrogen or alkyl of from 1 to 6 carbon atoms, $R_2$ is hydrogen, hydroxy, halogen, alkyl of from 1 to 6 carbon atoms or alkoxy of from 1 to 6 carbon atoms, and B is $SO_2NHR_6$ where $R_6$ is hydrogen or alkyl of from 1 to 6 carbon atoms; or (b) wherein A is a direct bond, $R_2$ is alkoxy of from 1 to 6 carbon atoms, and B is $SO_2NHR_6$ where $R_6$ is hydrogen or alkyl of from 1 to 6 carbon atoms; or (c) wherein A is a direct bond, $R_2$ is hydrogen, and B is $SO_2NHR_6$ where $R_6$ is

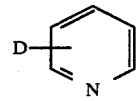

where D is an alkylene group of from 1 to 6 carbon atoms.

2. The compound defined in claim 1 which is N-[4-[2-(aminosulfonyl)ethenyl]phenyl-5-(2,5-dimethylphenoxy)-2,2-dimethylpentanamide, and the pharmaceutically acceptable salts thereof.

3. The compound defined in claim 1 which is N-[4-[2-N-t-butylaminosulfonyl)ethenyl]phenyl]-5-(2,5-dimethylphenoxy)-2,2-dimethylpentanamide, and the pharmaceutically salts thereof.

4. The compound defined in claim 1 which is N-[4-(N-(3-pyridylmethylamino)sulfonyl)phenyl]-5-(2,5-dimethylphenoxy)-2,2-dimethylpentanamide, and the pharmaceutically acceptable salts thereof.

5. The compound defined in claim 1 which is N-[3-(aminosulfonyl)-4-methoxyphenyl]-5-(2,5-dimethylphenoxy)-2,2-dimethylpentanamide, and the pharmaceutically acceptable salts thereof.

6. The compound defined in claim 1 which is 5-(2,5-dimethylphenoxy)-N-[4-methoxy-3-[(methylamino)sulfonyl]phenyl]-2,2-dimethylpentanamide, and the pharmaceutically acceptable salts thereof.

7. A pharmaceutical composition useful for treating arteriosclerosis in a mammal consisting essentially of an effective amount of a compound as defined in claim 1, or mixtures thereof, in combination with a pharmaceutically acceptable carrier.

8. A method for treating arteriosclerosis in a mammal in need of such treatment; which comprises administering an effective amount of the pharmaceutical composition defined in claim 7 to said mammal.

* * * * *